United States Patent
Kumar et al.

(10) Patent No.: US 9,752,154 B2
(45) Date of Patent: Sep. 5, 2017

(54) HIGH-THROUGHPUT DNA FRAGMENT ASSEMBLY

(71) Applicants: DOW AGROSCIENCES LLC, Indianapolis, IN (US); Sandeep Kumar, Carmel, IN (US); Steven L. Evans, Zionsville, IN (US); Manju Gupta, Carmel, IN (US)

(72) Inventors: Sandeep Kumar, Indianapolis, IN (US); Steven L. Evans, Indianapolis, IN (US); Manju Gupta, Indianapolis, IN (US)

(73) Assignee: Dow AgroSciences LLC, Indianapolis, IN (US)

(*) Notice: Subject to any disclaimer, the term of this patent is extended or adjusted under 35 U.S.C. 154(b) by 142 days.

(21) Appl. No.: 14/416,799

(22) PCT Filed: Jul. 23, 2013

(86) PCT No.: PCT/US2013/051641
§ 371 (c)(1),
(2) Date: Jan. 23, 2015

(87) PCT Pub. No.: WO2014/018512
PCT Pub. Date: Jan. 30, 2014

(65) Prior Publication Data
US 2015/0176015 A1 Jun. 25, 2015

Related U.S. Application Data

(60) Provisional application No. 61/675,929, filed on Jul. 26, 2012.

(51) Int. Cl.
*C12N 15/68* (2006.01)
*C12N 15/82* (2006.01)

(52) U.S. Cl.
CPC ......... *C12N 15/8209* (2013.01); *C12N 15/68* (2013.01); *C12N 15/82* (2013.01)

(58) Field of Classification Search
None
See application file for complete search history.

(56) References Cited

U.S. PATENT DOCUMENTS

2004/0229229 A1* 11/2004 Cheo .................. C07K 14/47
435/6.16
2012/0084885 A1* 4/2012 Alexandrov ....... C12N 15/8216
800/298

FOREIGN PATENT DOCUMENTS

WO    WO 2004098530 A2 * 11/2004 ......... C12N 15/8258

OTHER PUBLICATIONS

Li et al., Nature Methods, 2007, vol. 4, pp. 251-256.*

* cited by examiner

*Primary Examiner* — Mindy G Brown
(74) *Attorney, Agent, or Firm* — Yung H. Lee

(57) ABSTRACT

This invention is related to methods and systems for vector assembly for transgenic plants. A uniform modular process is used to reduce cycle time and the methods and systems provided herein can increase cloning throughput using multiple-well plates, for example 96-well plates. In some embodiments, the methods and systems provided herein eliminate or reduce the need for sequencing confirmation because no PCR is involved in the vector assembly process.

8 Claims, 13 Drawing Sheets

SEQ ID NO: 1 CCACACGACACCATG
SEQ ID NO: 2 CCAGAAGACACCATG
SEQ ID NO: 3 AAAGAGCCCGCCATG
SEQ ID NO: 4 AACCGCCCAGCCATG
SEQ ID NO: 5 AACGAGACCGAGATG
SEQ ID NO: 6 AAGAGCCCCAAGATG
SEQ ID NO: 7 ACAAGAGCCACCATG
SEQ ID NO: 8 ACAGGAACCACGATG
SEQ ID NO: 9 ACCCACGCAGAGATG
SEQ ID NO: 10 AGAACGACAAAGATG
SEQ ID NO: 11 AGCCGAACAACCATG
SEQ ID NO: 12 AGCCGAACAACGATG
SEQ ID NO: 13 CAAAGGCCCGCCATG
SEQ ID NO: 14 CAACGCCCAGCCATG
SEQ ID NO: 15 CACAGCCCCGAGATG
SEQ ID NO: 16 CACGGAACCAAGATG
SEQ ID NO: 17 CAGACAGCCACCATG
SEQ ID NO: 18 CAGACCCCACGATG
SEQ ID NO: 19 CAGGCGTCAGAGATG
SEQ ID NO: 20 CAGTGGCCAAAGATG
SEQ ID NO: 21 CCACCAGCAACCATG
SEQ ID NO: 22 CCCCAAGCAACGATG
SEQ ID NO: 23 CCCGACACCGCCATG

SEQ ID NO: 24 CGCACCACAGCCATG
SEQ ID NO: 25 CGGGTCACCGAGATG
SEQ ID NO: 26 GAAAGACCCAAGATG
SEQ ID NO: 27 GAAGACACCACCATG
SEQ ID NO: 28 GACACAGCCACGATG
SEQ ID NO: 29 GCAAAGACAGAGATG
SEQ ID NO: 30 GCAAAGACAAAGATG
SEQ ID NO: 31 GCCACCACAACCATG
SEQ ID NO: 32 GCGAAAACAACGATG
SEQ ID NO: 33 GCGCGTACCGCCATG
SEQ ID NO: 34 GGAACCACAGCCATG
SEQ ID NO: 35 GGCACAACCGAGATG
SEQ ID NO: 36 GGCCAAACCAAGATG
SEQ ID NO: 37 GGCTAGCCCACCATG
SEQ ID NO: 38 GGGCATCCCACGATG
SEQ ID NO: 39 GGTGCACCAGAGATG
SEQ ID NO: 40 GTCAGCGCAAAGATG
SEQ ID NO: 41 TGCGGCACAACCATG
SEQ ID NO: 42 TGGGACCCAACGATG
SEQ ID NO: 43 CCGGGGTCGACCATG

FIG. 3

SEQ ID NO: 44 TAATTAATTGA
SEQ ID NO: 45 TAATTAGTTAA
SEQ ID NO: 46 TAATTAGTTAG
SEQ ID NO: 47 TAATTAGTTGA
SEQ ID NO: 48 TAATTGATTGA
SEQ ID NO: 49 TAGTTAATTAA
SEQ ID NO: 50 TAGTTAATTAG
SEQ ID NO: 51 TAGTTAATTGA
SEQ ID NO: 52 TAGTTAGTTAA
SEQ ID NO: 53 TAGTTAGTTAG
SEQ ID NO: 54 TAGTTAGTTGA
SEQ ID NO: 55 TAGTTGATTAA
SEQ ID NO: 56 TAGTTGATTAG
SEQ ID NO: 57 TAGTTGATTGA
SEQ ID NO: 58 TGATTAATTGA
SEQ ID NO: 59 TGATTAGTTAA
SEQ ID NO: 60 TGATTAGTTAG
SEQ ID NO: 61 TGATTAGTTGA
SEQ ID NO: 62 TGATTGATTGA
SEQ ID NO: 63 tagttagttgaACACGACACCATG

FIG. 4

SEQ ID NO: 64 CTGCAGGTCGACATG
SEQ ID NO: 65 CTGCAGGTCGACATG
SEQ ID NO: 66 AAGTTTGTAGATCTCCATG
SEQ ID NO: 67 AAATGCGCAGATCCCCATG
SEQ ID NO: 68 AAAAAATG
SEQ ID NO: 69 CAAAAATG
SEQ ID NO: 70 AAAACATG
SEQ ID NO: 71 CAAACATG
SEQ ID NO: 72 AACAAATG
SEQ ID NO: 73 AAACAATG
SEQ ID NO: 74 AACCAATG

FIG. 5A

SEQ ID NO: 75 TGAGTAGTTAGCTTAATCACCTAGAGCTC
SEQ ID NO: 76 TAGGTAGTTAGCTTAATCACCTAGAGCTC
SEQ ID NO: 77 TAGGTAATTAGCTTAATCACCTAGAGCTC
SEQ ID NO: 78 TGAGTAGTTAGCTTAATCACCTAGAGCTC
SEQ ID NO: 79 TAAGTAGTTAGCTTAATCACCTAGAGCTC
SEQ ID NO: 80 TGAGTAATTAGCTTAATCACCTAGAGCTC

FIG. 5B

HIGH-THROUGHPUT DNA FRAGMENT ASSEMBLY

CROSS-REFERENCE TO RELATED APPLICATIONS

This application claims priority under 35 U.S.C. §119 of U.S. provisional patent application Ser. No. 61/675,929 filed Jul. 26, 2012, which application is hereby incorporated by reference in its entirety. This application is a national phase entry of international application PCT/US2013/051641 filed Jul. 23, 2013, which application is hereby incorporated by reference in its entirety.

FIELD OF THE INVENTION

This invention is generally related to the field of molecular biology, and more specifically the field of DNA fragment assembly to construct vector for transgenic plants.

BACKGROUND OF THE INVENTION

Several methodologies have been developed for introducing transgenes into plants to study gene functions. In general, these systems for producing transgenic plants have some common features: (1) a gene delivery system, (2) a selection system to differentiate transformed cells or plants from untransformed ones, and (3) a regeneration procedure to produce an entire plant (often fertile as well). Among all systems used, *Agrobacterium*-mediated gene transfer and particle bombardment (in tissue culture) have been popular in recent years to generate transgenic plants.

Traditionally, cloning of vectors for transgenic plants using restriction enzymes and ligases has been time consuming and labor intensive, partly because specific cis- and/or trans-elements are required for different plants, and often for different pant parts/tissues. Polymerase Chain Reaction (PCR) has been used extensively for cloning. However, vectors generated using PCR require sequencing confirmation due to the error-prone nature of PCR. Recently, site specific recombinases and transposases have been developed for general cloning. However, their application for vector assembly for transgenic plants has provided limited success.

Thus, there remains a need to provide a high-throughput vector assembly method for transgenic plants.

SUMMARY OF THE INVENTION

This invention is related to methods and systems for DNA fragment assembly to construct vector for transgenic plants. A uniform, modular, directional, and precise process for vector assembly is used to reduce cycle time and the methods and systems provided herein can increase cloning throughput using multiple-well plates, for example 96-well plates. In some embodiments, the methods and systems provided herein eliminate or reduce the need for sequencing confirmation because no PCR is involved in the vector assembly process.

In one aspect, provided is a method for directional DNA fragment assembly. The method comprises:
(a) PCR amplifying, synthesizing or digesting a plasmid with at least one type II restriction enzyme to obtain a first DNA molecule, wherein the first DNA molecule comprises a Kozak sequence;
(b) PCR amplifying, synthesizing or digesting a plasmid with at least one type II restriction enzyme to obtain a second DNA molecule, wherein the second DNA molecule comprises a Kozak sequence at one end and a six frame stop sequence at the other end;
(c) PCR amplifying, synthesizing or digesting a plasmid with at least one type II restriction enzyme to obtain a third DNA molecule, wherein the third DNA molecule comprises a six-frame stop sequence;
(d) PCR amplifying, synthesizing or digesting a plasmid with at least one type II restriction enzyme to obtain a fourth DNA molecule, wherein the fourth DNA molecule comprises a vector sequence; and
(e) assembling product vector using digested products of steps (a), (b), (c), and (d) in the presence of at least one recombinase.

In another aspect, provided is a method for precise and directional DNA fragment assembly. The method comprises:
(a) PCR amplifying, synthesizing or digesting a plasmid with at least one type II restriction enzyme to generate DNA fragment 1, wherein the DNA fragment 1 is flanked by a 5' vector homology sequence and a Kozak sequence;
(b) PCR amplifying, synthesizing or digesting a plasmid with at least one type II restriction enzyme to generate DNA fragment 2, wherein the DNA fragment 2 is flanked by a Kozak sequence and a six-frame stop sequence;
(c) PCR amplifying, synthesizing or digesting a plasmid with at least one type II restriction enzyme to generate DNA fragment 3, wherein the DNA fragment 3 is flanked by a six-frame stop sequence and a 3' vector homology sequence;
(d) PCR amplifying, synthesizing or digesting a plasmid with at least one type II restriction enzyme to generate DNA fragment 4, wherein the DNA fragment 4 comprises a vector sequence flanked by a 3' vector homology sequence and a 5' vector homology sequence; and
(e) assembling product vector using the DNA fragments 1, 2, 3, and 4 in the presence of at least one recombinase.

In one embodiment of the methods provided, the method further comprises treating the digested products of steps (a), (b), (c), and (d) with an enzyme with 3' to 5' exonuclease activity. In another embodiment, no DNA amplification technique is used. In a further embodiment, polymerase chain reaction is not used.

In another embodiment, the type II restriction enzyme is selected from the group consisting of AcuI, BciVI, BmrI, BseRI, BsrDI, BtsI, MlyI, and combinations thereof. In another embodiment, the fourth DNA molecule comprises a lethal gene. In a further embodiment, the lethal gene is ccdB. In another embodiment, the Kozak sequence has at least 80%, 85%, 90%, 95%, or 100% identity to SEQ ID NOS 1-43, 64-74, or their complements. In a further embodiment, the Kozak sequence is selected from the group consisting of 1-43, 64-74, and their complements. In another embodiment, the Kozak sequence comprises a three-frame stop sequence at its 5' end. In a further embodiment, the three-frame stop sequence is from the group consisting of SEQ ID NOS 44-62 and their complements. In another embodiment, the six frame stop sequence has at least 80%, 85%, 90%, 95%, or 100% identity to SEQ ID NOS 75-80 or their complements. In a further embodiment, the six frame stop sequence is selected from the group consisting of SEQ ID NOS 75-80 and their complements.

In another embodiment, the recombinase is selected from the group consisting of Int, Cre, Flp, IHF, Xis, γδ, Tn3 resolvase, Hin, Gin, Cin, Fis, TndX, XerC, XerD, and Res.

In another embodiment, the recombinase is not a site-specific recombinase. In another embodiment, the recombinase does not comprise a protein encoded by a bacteriophage. In a further embodiment, the bacteriophage is selected from the group consist of lambda, phi80, P22, P2, 186, P4, and P1. In another embodiment, the digested product of the fourth DNA molecule comprises a selectable marker. In a further embodiment, the selectable marker comprises an antibiotic resistance gene. In a further or alternative embodiment, the selectable marker is selected from the group consisting of kanamycin and ampicillin resistance genes. In another embodiment, steps (a)-(e) are performed in vitro. In another embodiment, the assembled product vector is for use in transgenic plants. In a further or alternative embodiment, the assembled product vector is a binary vector for *Agrobacterium*-mediated transformation. In another embodiment, the assembled product vector does not comprises a recombination sites selected from the group consisting of lox sites, psi sites, dif sites, cer sites, frt sites, att sites, and combinations thereof.

In another aspect, provided is a system for DNA fragment assembly to construct vector. The system comprises:
(a) DNA fragment 1 digested from a first DNA molecule using at least one type II restriction enzyme, wherein the DNA fragment 1 comprises a Kozak sequence;
(b) DNA fragment 2 digested from a second DNA molecule using at least one type II restriction enzyme, wherein the DNA fragment 2 comprises a Kozak sequence at one end and a six frame stop sequence at the other end;
(c) DNA fragment 3 digested from a third DNA molecule using at least one type II restriction enzyme, wherein the DNA fragment 3 comprises a six frame stop sequence;
(d) DNA fragment 4 digested from a fourth DNA molecule using at least one type II restriction enzyme, wherein the DNA fragment 4 comprises a vector sequence; and
(e) at least one recombinase to assemble a product vector using DNA fragments 1, 2, 3, and 4.

In another aspect, provided is a system for vector assembly. The system comprises:
(a) DNA fragment 1 digested from a first DNA molecule using at least one type II restriction enzyme, wherein the DNA fragment 1 is flanked by a 5' vector homology sequence and a Kozak sequence;
(b) DNA fragment 2 digested from a second DNA molecule using at least one type II restriction enzyme, wherein the DNA fragment 2 is flanked by a Kozak sequence and a six frame stop sequence;
(c) DNA fragment 3 digested from a third DNA molecule using at least one type II restriction enzyme, wherein the DNA fragment 3 is flanked by a six frame stop sequence and a 3' vector homology sequence;
(d) DNA fragment 4 digested from a fourth DNA molecule using at least one type II restriction enzyme, wherein the DNA fragment 4 comprises a vector sequence flanked by a 3' vector homology sequence and a 5' vector homology sequence; and
(e) at least one recombinase to assemble a product vector using DNA fragments 1, 2, 3, and 4.

In one embodiment of the systems provided, the system further comprises an enzyme with 3' to 5' exonuclease activity. In another embodiment, no DNA amplification technique is used. In a further embodiment, polymerase chain reaction is not used.

In one embodiment, the type II restriction enzyme is selected from the group consisting of AcuI, BciVI, BmrI, BseRI, BsrDI, BtsI, MlyI, and combinations thereof.

In one embodiment, the recombinase is selected from the group consisting of Int, Cre, Flp, IHF, Xis, $\gamma_6$, Tn3 resolvase, Hin, Gin, Cin, Fis, TndX, XerC, XerD, and Res. In another embodiment, the recombinase is not a site-specific recombinase. In another embodiment, the recombinase does not comprise a protein encoded by a bacteriophage. In a further embodiment, the bacteriophage is selected from the group consist of lambda, phi80, P22, P2, 186, P4, and P1. In another embodiment, the DNA fragment 4 comprises a selectable marker. In a further embodiment, the selectable marker comprises an antibiotic resistance gene. In a further or alternative embodiment, the selectable marker is selected from the group consisting of kanamycin and ampicillin resistance genes. In another embodiment, the assembled product vector is for use in transgenic plants. In a further or alternative embodiment, the assembled product vector is a binary vector for *Agrobacterium*-mediated transformation. In another embodiment, the assembled product vector does not comprises a recombination sites selected from the group consisting of lox sites, psi sites, dif sites, cer sites, frt sites, att sites, and combinations thereof.

BRIEF DESCRIPTION OF THE DRAWINGS

FIG. 3 shows a list of exemplary Kozak sequences (SEQ ID NOS: 1-43).

FIG. 4 shows a list of exemplary three-frame stop sequences (SEQ ID NOS 44-62) which can be linked to a Kozak sequence. SEQ ID NO: 63 shows an exemplary Kozak plus a three-frame stop sequence.

FIG. 5A shows a list of exemplary dicot Kozak sequences. FIG. 5B shows a list of exemplary six-frame stop sequences (SEQ ID NO: 75-80).

Promoter and CDS fragments contain Kozak sequence comprising a three-frame stop sequence at its 5' end. The four fragments are assembled into an expression vector in one step.

Figure 11:
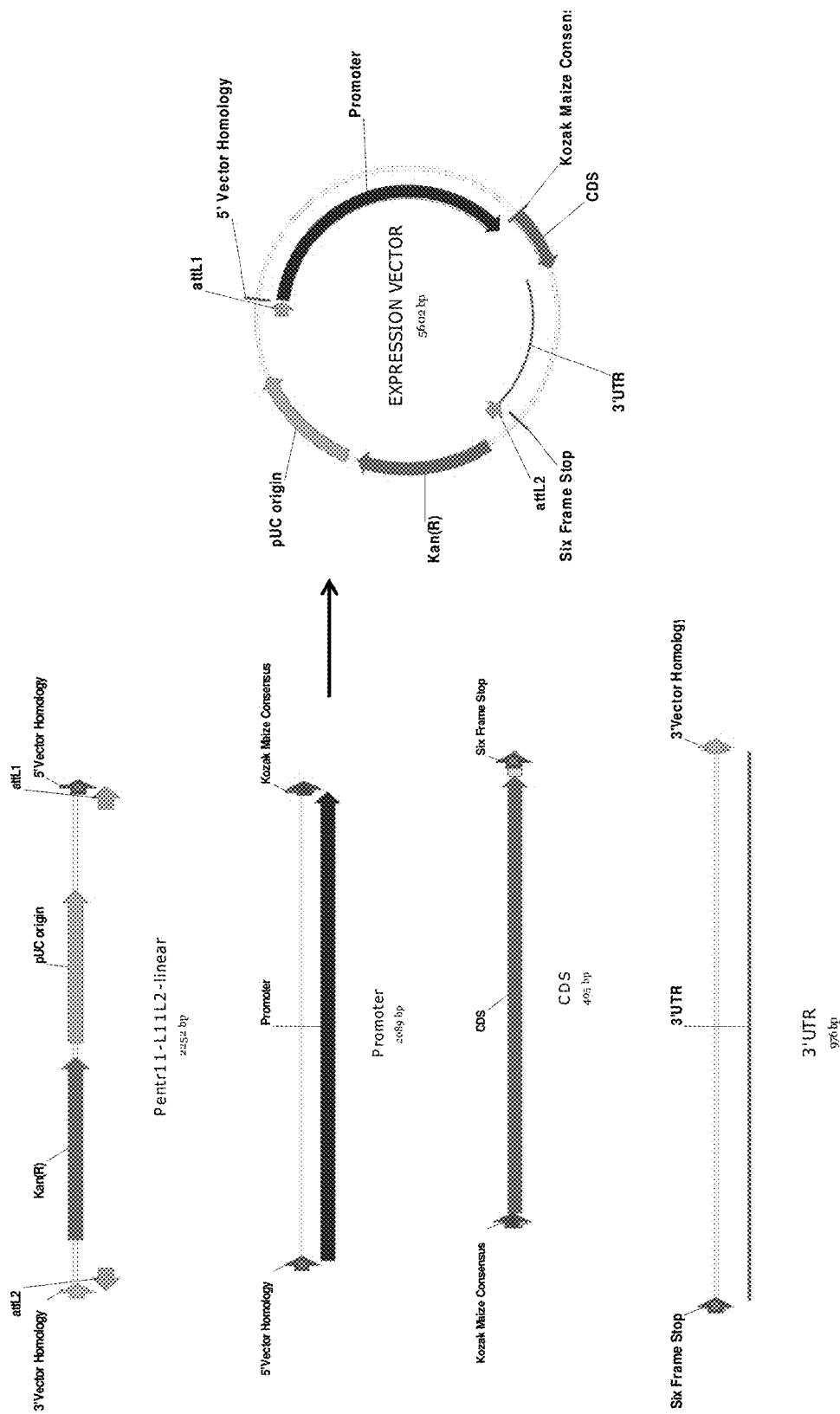

FIG. 11 shows exemplary vector assembly using methods and/or systems provided herein. The four fragments are assembled into an expression vector in one step.

DETAILED DESCRIPTION OF THE INVENTION

The production of transgenic plants has become routine for many plant species, but the current methodologies are labor intensive. Thus, a goal of the methods and systems disclosed is to provide a vector assembly method suitable for high-throughput applications in a consistent and/or concise manner.

In conventional gene cloning, suitable restriction enzymes are identified based on the sequence of the target gene before it can be inserted into a vector plasmid. Both vector DNA and the gene inserts are typically cut with the same restriction enzyme(s) and then ligated together with DNA ligase. This process requires manual handling of DNA fragments, which requires the insertion of undesirable multiple cloning site sequences, more specifically between the promoter and coding sequences that might affect gene expression. In addition, the coding sequence or genetic elements may sometimes contain internal restriction sites that are also recognized by the chosen enzyme, and these require modifications prior to cloning. Thus, a more efficient and effective vector assembly process is needed to be adaptable for high-throughput cloning/applications.

Provided are methods and systems for vector assembly using specific sequence junctions which are uniform among all the vectors for a given organism. The design of the methods and systems provided enable high-throughput cloning/applications in contract to previously known cloning methods. For example, a Kozak/consensus sequence (Kozak M., 1991) and a stop codon (in more than one frame) at the 5' and 3' ends of the coding sequence and the same sequence at ends of their adjacent DNA fragments can be used for vectors designed for transgenic plants. These sequences while providing critical biological function for stable gene expression also serve as vital sequence homologies required for linear DNA fragment assembly using DNA recombination technologies.

Provided is a fast-track and high-throughput (HTP) process of assembling DNA fragments into a functional transcriptional unit, without any undesired intervening sequences. The process utilized unique organism-specific small sequences on 5' and 3' junctions of the coding region. These unique junction micro-homologies are used for assembling promoter, coding sequence and 3'UTR in a desired orientation. The unique Kozak/consensus sequence can be inserted on the 5' junction while six frame stop codon can be added on 3' of the coding sequence. The insertion of Kozak/consensus sequence on the 3' of promoter and addition of six frame stop codon on the 5' of the 3'UTR provides required junction homologies for making HTP vectors using DNA recombination technologies.

In some embodiments, provided is the use of type II restriction enzymes to extract DNA fragments from plasmids for vector assembly provided herein. The type II restriction enzymes (see Table 1) that give blunt or short 3' overhangs are used for this invention. The 3' to 5' exonuclease activity of the seamless cloning or similar enzyme makes fragments blunt during the cloning process. The invention also describes the use of lethal gene, e.g., ccdB, in the vector that is used for backbone extraction. In addition, a selection marker is used on the backbone that is different than vectors that are used to extract fragments for seamless assembly. The negative selection marker on backbone vector will avoid background clones for potential uncut backbone vector while different selection marker on fragment vectors will prevent background from uncut fragment vector contamination.

The use of type II restriction enzymes to extract cloning compatible DNA fragments directly from the plasmid eliminates need of PCR amplification. DNA fragments can be assembled into desired product vector flanked by type II restriction enzyme site on both ends such that a small 3' overhang or blunt end fragment is released after plasmid restriction. Provided is a platform to extract and build a library of compatible fragments to make technology modular, high-throughput and automated. In some embodiment, use of a negative selection marker in the donor vectors/plasmid is provided, where vector backbone of the product vector can comprise positive selection markers. These embodiments prevent the background from potential uncut vector and enable the methods and systems provided more efficient under certain circumstances.

As used herein, the phrase "vector" refers to a piece of DNA, typically double-stranded, which can have inserted into it a piece of foreign DNA. The vector can be for example, of plasmid or viral origin, which typically encodes a selectable or screenable marker or transgenes. The vector is used to transport the foreign or heterologous DNA into a suitable host cell. Once in the host cell, the vector can replicate independently of or coincidental with the host chromosomal DNA. Alternatively, the vector can target insertion of the foreign or heterologous DNA into a host chromosome.

As used herein, the phrase "transgene vector" refers to a vector that contains an inserted segment of DNA, the "transgene" that is transcribed into mRNA or replicated as a RNA within a host cell. The phrase "transgene" refers not only to that portion of inserted DNA that is converted into RNA, but also those portions of the vector that are necessary for the transcription or replication of the RNA. A transgene typically comprises a gene-of-interest but needs not necessarily comprise a polynucleotide sequence that contains an open reading frame capable of producing a protein.

As used herein, the phrase "transformed" or "transformation" refers to the introduction of DNA into a cell. The phrases "transformant" or "transgenic" refers to plant cells, plants, and the like that have been transformed or have undergone a transformation procedure. The introduced DNA is usually in the form of a vector containing an inserted piece of DNA.

As used herein, the phrase "selectable marker" or "selectable marker gene" refers to a gene that is optionally used in plant transformation to, for example, protect the plant cells from a selective agent or provide resistance/tolerance to a selective agent. Only those cells or plants that receive a functional selectable marker are capable of dividing or growing under conditions having a selective agent. Examples of selective agents can include, for example, antibiotics, including spectinomycin, neomycin, kanamycin, paromomycin, gentamicin, and hygromycin. These selectable markers include gene for neomycin phosphotransferase (npt II), which expresses an enzyme conferring resistance to the antibiotic kanamycin, and genes for the related antibiotics neomycin, paromomycin, gentamicin, and G418, or the gene for hygromycin phosphotransferase (hpt), which expresses an enzyme conferring resistance to hygromycin. Other selectable marker genes can include genes encoding herbicide resistance including Bar (resistance against BASTA® (glufosinate ammonium), or phosphinothricin (PPT)), acetolactate synthase (ALS, resistance against inhibitors such as sulfonylureas (SUs), imidazolinones (IMIs), triazolopyrimidines (TPs), pyrimidinyl oxybenzoates (POBs), and sulfonylamino carbonyl triazolinones that prevent the first step in the synthesis of the branched-chain amino acids), glyphosate, 2,4-D, and metal resistance or sensitivity. The phrase "marker-positive" refers to plants that have been transformed to include the selectable marker gene.

Various selectable or detectable markers can be incorporated into the chosen expression vector to allow identification and selection of transformed plants, or transformants. Many methods are available to confirm the expression of selection markers in transformed plants, including for example DNA sequencing and PCR (polymerase chain reaction), Southern blotting, RNA blotting, immunological methods for detection of a protein expressed from the vector, e.g., precipitated protein that mediates phosphinothricin resistance, or other proteins such as reporter genes β-glucuronidase (GUS), luciferase, green fluorescent protein (GFP), DsRed, β-galactosidase, chloramphenicol acetyltransferase (CAT), alkaline phosphatase, and the like (See Sambrook, et al., Molecular Cloning: A Laboratory Manual, Third Edition, Cold Spring Harbor Press, N.Y., 2001, the content of which is incorporated herein by reference in its entirety).

Selectable marker genes are utilized for the selection of transformed cells or tissues. Selectable marker genes include genes encoding antibiotic resistance, such as those encoding neomycin phosphotransferase II (NEO) and hygromycin phosphotransferase (HPT) as well as genes conferring resistance to herbicidal compounds. Herbicide resistance genes generally code for a modified target protein insensitive to the herbicide or for an enzyme that degrades or detoxifies the herbicide in the plant before it can act. See DeBlock et al. (1987) EMBO J., 6:2513-2518; DeBlock et al. (1989) Plant Physiol., 91:691-704; Fromm et al. (1990) 8:833-839; Gordon-Kamm et al. (1990) 2:603-618). For example, resistance to glyphosate or sulfonylurea herbicides has been obtained by using genes coding for the mutant target enzymes, 5-enolpyruvylshikimate-3-phosphate synthase (EPSPS) and acetolactate synthase (ALS). Resistance to glufosinate ammonium, bromoxynil, and 2,4-dichlorophenoxyacetate (2,4-D) have been obtained by using bacterial genes encoding phosphinothricin acetyltransferase, a nitrilase, or a 2,4-dichlorophenoxyacetate monooxygenase, which detoxify the respective herbicides. Enzymes/genes for 2,4-D resistance have been previously disclosed in US 2009/0093366 and WO 2007/053482, the contents of which are hereby incorporated by reference in their entireties.

Other herbicides can inhibit the growing point or meristem, including imidazolinone or sulfonylurea. Exemplary genes in this category code for mutant ALS and AHAS enzyme as described, for example, by Lee et al., EMBO J. 7:1241 (1988); and Miki et al., Theon. Appl. Genet. 80:449 (1990), respectively.

Glyphosate resistance genes include mutant 5-enolpyruvylshikimate-3-phosphate synthase (EPSPs) genes (via the introduction of recombinant nucleic acids and/or various forms of in vivo mutagenesis of native EPSPs genes), aroA genes and glyphosate acetyl transferase (GAT) genes, respectively). Resistance genes for other phosphono compounds include glufosinate (phosphinothricin acetyl transferase (PAT) genes from *Streptomyces* species, including *Streptomyces hygroscopicus* and *Streptomyces viridichromogenes*), and pyridinoxy or phenoxy proprionic acids and cyclohexones (ACCase inhibitor-encoding genes), See, for example, U.S. Pat. No. 4,940,835 to Shah, et al. and U.S. Pat. No. 6,248,876 to Barry et al., which disclose nucleotide sequences of forms of EPSPs which can confer glyphosate resistance to a plant. A DNA molecule encoding a mutant aroA gene can be obtained under ATCC accession number 39256, and the nucleotide sequence of the mutant gene is disclosed in U.S. Pat. No. 4,769,061 to Comai, European patent application No. 0 333 033 to Kumada et al., and U.S. Pat. No. 4,975,374 to Goodman et al., disclosing nucleotide sequences of glutamine synthetase genes which confer resistance to herbicides such as L-phosphinothricin. The nucleotide sequence of a PAT gene is provided in European application No. 0 242 246 to Leemans et al. Also DeGreef et al., Bio/Technology 7:61 (1989), describes the production of transgenic plants that express chimeric bar genes coding for PAT activity. Exemplary of genes conferring resistance to phenoxy proprionic acids and cyclohexones, including sethoxydim and haloxyfop, are the Acc1-S1, Acc1-S2 and Acc1-S3 genes described by Marshall et al., Theon. Appl. Genet. 83:435 (1992). GAT genes capable of conferring glyphosate resistance are described in WO 2005012515 to Castle et al. Genes conferring resistance to 2,4-D, fop and pyridyloxy auxin herbicides are described in WO 2005107437 and U.S. patent application Ser. No. 11/587,893.

Other herbicides can inhibit photosynthesis, including triazine (psbA and 1s+ genes) or benzonitrile (nitrilase gene). Przibila et al., Plant Cell 3:169 (1991), describes the transformation of *Chlamydomonas* with plasmids encoding mutant psbA genes. Nucleotide sequences for nitrilase genes are disclosed in U.S. Pat. No. 4,810,648 to Stalker, and DNA molecules containing these genes are available under ATCC Accession Nos. 53435, 67441, and 67442. Cloning and expression of DNA coding for a glutathione S-transferase is described by Hayes et al., Biochem. J. 285:173 (1992).

For purposes of the present invention, selectable marker genes include, but are not limited to genes encoding: neomycin phosphotransferase II (Fraley et al. (1986) CRC Critical Reviews in Plant Science, 4:1-25); cyanamide hydratase (Maier-Greiner et al. (1991) Proc. Natl. Acad. Sci. USA, 88:4250-4264); aspartate kinase; dihydrodipicolinate synthase (Perl et al. (1993) Bio/Technology, 11:715-718); tryptophan decarboxylase (Goddijn et al. (1993) Plant Mol. Bio., 22:907-912); dihydrodipicolinate synthase and desensitized aspartate kinase (Perl et al. (1993) Bio/Technology, 11:715-718); bar gene (Told et al. (1992) Plant Physiol., 100:1503-1507 and Meagher et al. (1996) and Crop Sci., 36:1367); tryptophan decarboxylase (Goddijn et al. (1993) Plant Mol. Biol., 22:907-912); neomycin phosphotransferase (NEO) (Southern et al. (1982) J. Mol. Appl. Gen., 1:327; hygromycin phosphotransferase (HPT or HYG) (Shimizu et al. (1986) Mol. Cell Biol., 6:1074); dihydrofolate reductase (DHFR) (Kwok et al. (1986) PNAS USA 4552); phosphinothricin acetyltransferase (DeBlock et al. (1987) EMBO J., 6:2513); 2,2-dichloropropionic acid dehalogenase (Buchanan-Wollatron et al. (1989) J. Cell. Biochem. 13D:330); acetohydroxyacid synthase (Anderson et al., U.S. Pat. No. 4,761,373; Haughn et al. (1988) Mol. Gen. Genet. 221:266); 5-enolpyruvyl-shikimate-phosphate synthase (aroA) (Comai et al. (1985) Nature 317:741); haloarylnitrilase (Stalker et al., published PCT application WO87/04181); acetyl-coenzyme A carboxylase (Parker et al. (1990) Plant Physiol. 92:1220); dihydropteroate synthase (sul I)

(Guerineau et al. (1990) Plant Mol. Biol. 15:127); and 32 kD photosystem II polypeptide (psbA) (Hirschberg et al. (1983) Science, 222:1346).

Also included are genes encoding resistance to: chloramphenicol (Herrera-Estrella et al. (1983) EMBO J., 2:987-992); methotrexate (Herrera-Estrella et al. (1983) Nature, 303:209-213; Meijer et al. (1991) Plant Mol Bio., 16:807-820 (1991); hygromycin (Waldron et al. (1985) Plant Mol. Biol., 5:103-108; Zhijian et al. (1995) Plant Science, 108:219-227 and Meijer et al. (1991) Plant Mol. Bio. 16:807-820); streptomycin (Jones et al. (1987) Mol. Gen. Genet., 210:86-91); spectinomycin (Bretagne-Sagnard et al. (1996) Transgenic Res., 5:131-137); bleomycin (Hille et al. (1986) Plant Mol. Biol., 7:171-176); sulfonamide (Guerineau et al. (1990) Plant Mol. Bio., 15:127-136); bromoxynil (Stalker et al. (1988) Science, 242:419-423); 2,4-D (Streber et al. (1989) Bio/Technology, 7:811-816); glyphosate (Shaw et al. (1986) Science, 233:478-481); and phosphinothricin (DeBlock et al. (1987) EMBO J., 6:2513-2518). All references recited in the disclosure are hereby incorporated by reference in their entireties unless stated otherwise.

The above list of selectable marker and reporter genes are not meant to be limiting. Any reporter or selectable marker gene are encompassed by the present invention. If necessary, such genes can be sequenced by methods known in the art.

The reporter and selectable marker genes are synthesized for optimal expression in the plant. That is, the coding sequence of the gene has been modified to enhance expression in plants. The synthetic marker gene is designed to be expressed in plants at a higher level resulting in higher transformation efficiency. Methods for synthetic optimization of genes are available in the art. In fact, several genes have been optimized to increase expression of the gene product in plants.

The marker gene sequence can be optimized for expression in a particular plant species or alternatively can be modified for optimal expression in plant families. The plant preferred codons may be determined from the codons of highest frequency in the proteins expressed in the largest amount in the particular plant species of interest. See, for example, EPA 0359472; EPA 0385962; WO 91/16432; Perlak et al. (1991) Proc. Natl. Acad. Sci. USA, 88:3324-3328; and Murray et al. (1989) Nucleic Acids Research, 17:477-498; U.S. Pat. No. 5,380,831; and U.S. Pat. No. 5,436,391; herein incorporated by reference. In this manner, the nucleotide sequences can be optimized for expression in any plant. It is recognized that all or any part of the gene sequence may be optimized or synthetic. That is, fully optimized or partially optimized sequences may also be used.

In addition, several transformation strategies utilizing the *Agrobacterium*-mediated transformation system have been developed. For example, the binary vector strategy is based on a two-plasmid system where T-DNA is in a different plasmid from the rest of the Ti plasmid. In a co-integration strategy, a small portion of the T-DNA is placed in the same vector as the foreign gene, which vector subsequently recombines with the Ti plasmid.

As used herein, the phrase "plant" includes dicotyledons plants and monocotyledons plants. Examples of dicotyledons plants include tobacco, Arabidopsis, soybean, tomato, papaya, canola, sunflower, cotton, alfalfa, potato, grapevine, pigeon pea, pea, Brassica, chickpea, sugar beet, rapeseed, watermelon, melon, pepper, peanut, pumpkin, radish, spinach, squash, broccoli, cabbage, carrot, cauliflower, celery, Chinese cabbage, cucumber, eggplant, and lettuce. Examples of monocotyledons plants include corn, rice, wheat, sugarcane, barley, rye, sorghum, orchids, bamboo, banana, cattails, lilies, oat, onion, millet, and triticale.

As used herein the phrase "host" refers to any prokaryotic or eukaryotic organism that can be a recipient of the recombinational cloning Product. Accordingly, a "host" includes prokaryotic or eukaryotic organisms that can be genetically engineered. For examples of such hosts, see Maniatis et al., Molecular Cloning: A Laboratory Manual, Cold Spring Harbor Laboratory, Cold Spring Harbor, N.Y. (1982).

As used herein, the phrase "insert" or "inserts" refers to desired nucleic acid segment or a population of nucleic acid segments which may be manipulated by known methods of molecular biology. Thus, the terms Insert(s) are meant to include a particular nucleic acid (preferably DNA) segment or a population of segments. Such Insert(s) can comprise one or more genes/elements.

As used herein, the phrase "insert donor" refers to one of the two parental nucleic acid molecules (e.g. RNA or DNA) which carries the insert. The insert donor molecule comprises the insert flanked on both sides with specific sites. The insert donor can be linear or circular. In one embodiment of the invention, the insert donor is a circular DNA molecule and further comprises a cloning vector sequence. When a population of inserts or population of nucleic acid segments are used to make the insert donor, a population of insert donors result and may be used in accordance with the methods and/or systems provided herein.

As used herein, the phrase "product" or "product vector" refers to the desired daughter molecule after the vector assembly process described herein. The product contains the nucleic acid which is to be cloned or subcloned. In accordance with the invention, when a population of insert donors is used, the resulting population of product molecules will contain all or a portion of the population of inserts of the insert donors and preferably will contain a representative population of the original molecules of the insert donors.

As used herein, the phrase "promoter" refers to a DNA sequence generally described as the 5'-region of a gene, located proximal to the start codon. The transcription of an adjacent DNA segment is initiated at the promoter region. A repressible promoter's rate of transcription decreases in response to a repressing agent. An inducible promoter's rate of transcription increases in response to an inducing agent. A constitutive promoter's rate of transcription is not specifically regulated, though it can vary under the influence of general metabolic conditions.

As used herein, the phrase "site-specific recombinase" refers to a type of recombinase which typically has at least the following four activities (or combinations thereof): (1) recognition of one or two specific nucleic acid sequences; (2) cleavage of said sequence or sequences; (3) topoisomerase activity involved in strand exchange; and (4) ligase activity to reseal the cleaved strands of nucleic acid. See Sauer, B., Current Opinions in Biotechnology 5:521-527 (1994). Conservative site-specific recombination is distinguished from homologous recombination and transposition by a high degree of specificity for both partners. The strand exchange mechanism involves the cleavage and rejoining of specific DNA sequences in the absence of DNA synthesis. See Landy, A. (1989) Ann. Rev. Biochem. 58:913-949.

As used herein, the phrase "vector" refers to a nucleic acid molecule (preferably DNA) that provides a useful biological or biochemical property to an insert. Examples include plasmids, phages, autonomously replicating sequences (ARS), centromeres, and other sequences which are able to replicate or be replicated in vitro or in a host cell, or to convey a desired nucleic acid segment to a desired location within a host cell. A Vector can have one or more restriction endonuclease recognition sites at which the sequences can be cut in a determinable fashion without loss of an essential biological function of the vector, and into which a nucleic acid fragment can be spliced in order to bring about its replication and cloning. Vectors can further provide primer sites, e.g., for PCR, transcriptional and/or translational initiation and/or regulation sites, recombinational signals, replicons, selectable markers, etc. The cloning vector can further contain one or more selectable markers suitable for use in the identification of cells transformed with the cloning vector.

Provided are methods and systems by which modularity can be added to micro-homologies of DNA fragments such that multiple DNA fragments can be mixed and matched without having to re-synthesize DNA fragments each time. Sequences providing similar biological functions can be used as homology regions for DNA combinations. In some embodiments, Kozak consensus sequence homology between the promoter and coding sequence adjacent ends and a stop codon (in more than one frame) homology between the coding sequence and 3' UTR adjacent ends are use to assemble new plant transcription units (PTU). Similarly, use of micro-homologies of restriction enzyme recognition sites at both termini of a PTU is provided to simultaneously assemble it into a plasmid. The methods and systems provided enable directional, precise and high-throughput assembly of PTUs for vector construction that is functionally compatible with transgene expression.

The methods and systems provided are useful to create a high-throughput, flexible, modular DNA assembly platform allowing vector assembly/construction without need of adding any undesired or extra sequences in the vector. The methods and systems provided enable mixing and matching of existing modular DNA fragment to construct vectors with desired genetic elements. The methods and systems provided further enable directional, precise and high-throughput assembly of PTUs for vector construction that is functionally compatible with transgene expression.

EXAMPLES

Example 1—Modular Approach for Vector Assembly

Figure 1:
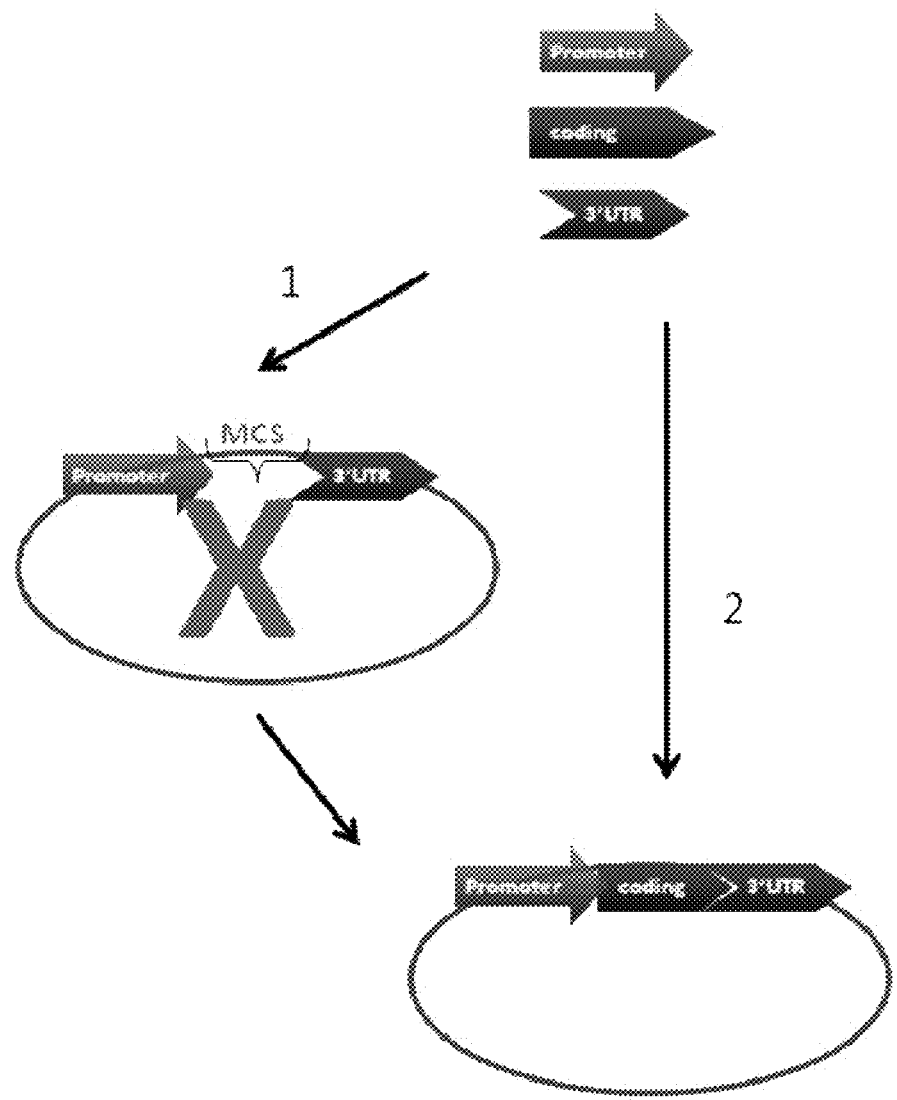
FIG. 1 shows comparison between traditional cloning using multiple-cloning site (MCS; pathway 1) and high-throughput vector assembly provided herein (pathway 2).

FIG. 1 illustrates difference before a traditional cloning method (path 1) and a modular approach provided herein (path 2). The modular approach provided has essentially less steps involved and is adaptable to a high-throughput format.

Figure 2A:
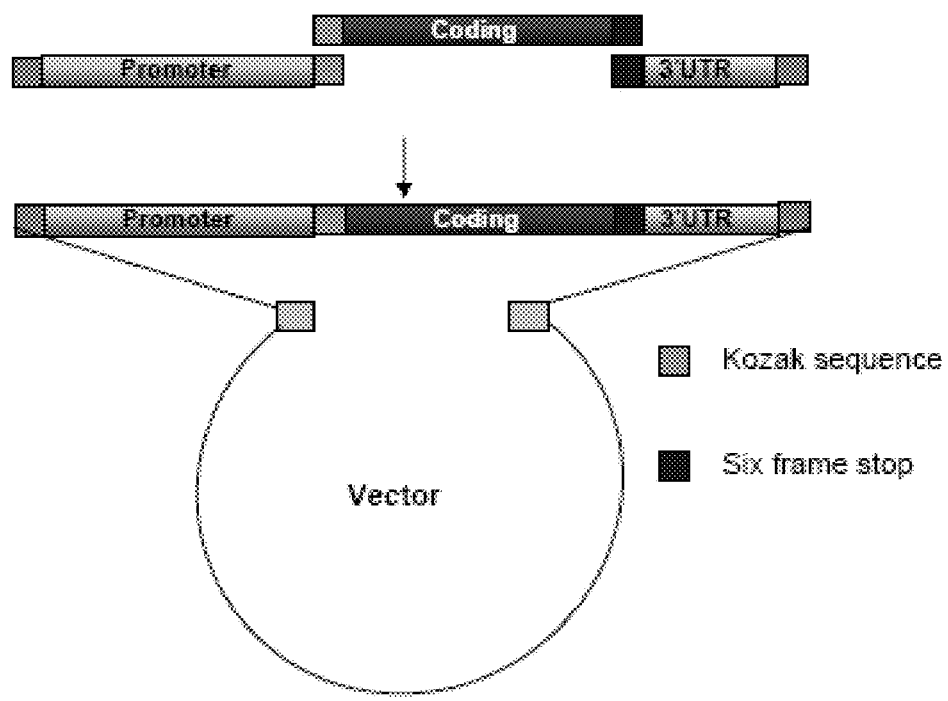
FIG. 2A shows an exemplary embodiment of the methods and systems provided herein. Kozak sequence is present in both the first and second fragments, and the six frame stop sequence is present in both second and third fragments. The fragments can be obtained using various approaches including PCR generated fragments.

Provided is a modular yet highly efficient vector construction approach for simultaneous, precise, and directional assembly of DNA fragments. An exemplary assembly process provided is illustrated in FIG. 2A. The DNA fragments can be either PCR amplified, synthesized, or cut from the existing plasmids. A Kozak sequence is inserted at the 5' while amino acid stop codons is added at the 3' ends of the coding sequence. The promoter fragment (fragment 1) contains a Kozak sequence at its 3' end and a small sequence at its 5' end matching a vector junction. The coding fragment (fragment 2) contains the Kozak sequence at its 5' junction and amino acid stop codons (in more than one frame) sequence at its 3' end. Similarly, the 3'UTR fragment (fragment 3) contains the amino acid stop codons (in more than one frame) sequence at its 5' end of 3' UTR and another small sequence matching another vector junction. The vector fragment (fragment 4) has two different vector junction sequences identical to corresponding sequences in fragments 1 and 3. Combining these modular linear fragments in the presence of suitable DNA recombination system will precisely assemble final vector containing these four fragments without any undesired sequences within the transcription unit.

Figure 2B:
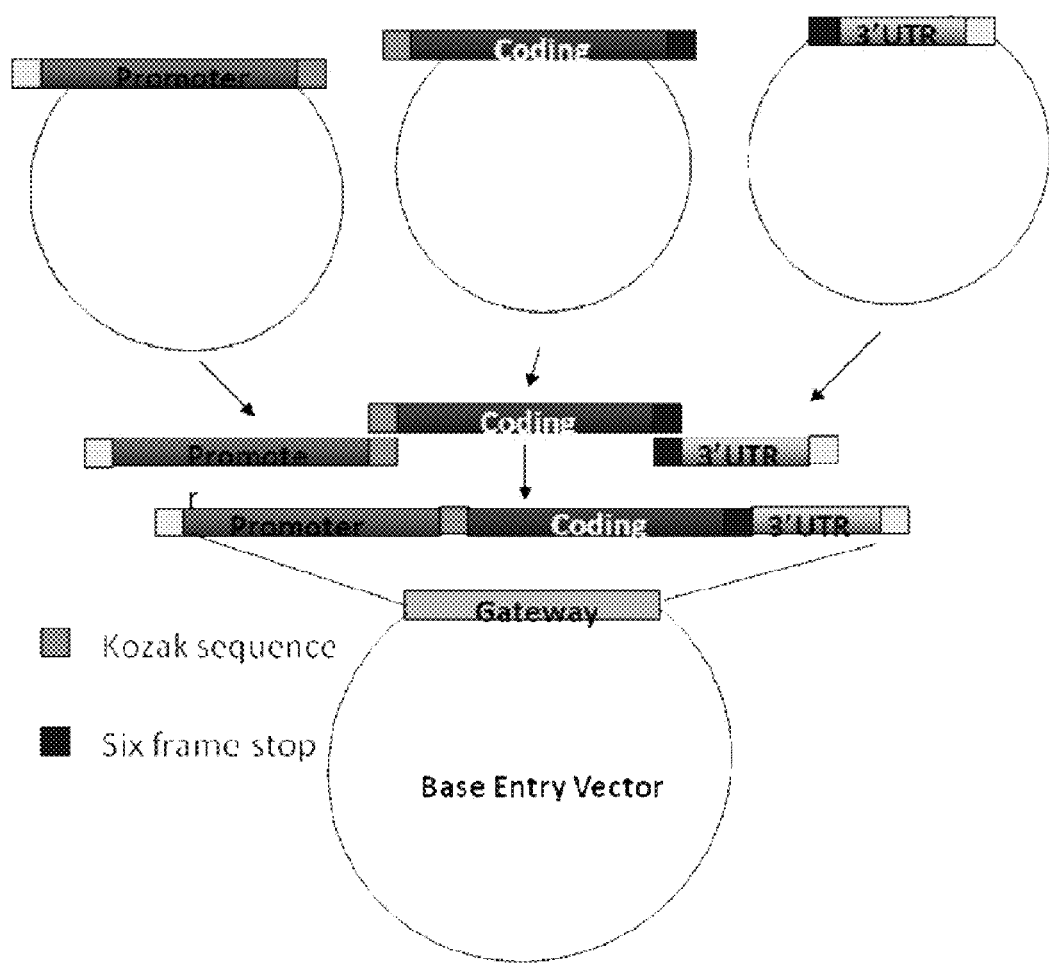
FIG. 2B shows another exemplary embodiment of the methods and systems provided herein, where fragments are generated using type II restriction enzymes from different plasmids. Kozak sequence is present in both the first and second fragments, and the six frame stop sequence is present in both second and third fragments. The fragments are not generated using PCR.
Figure 6:
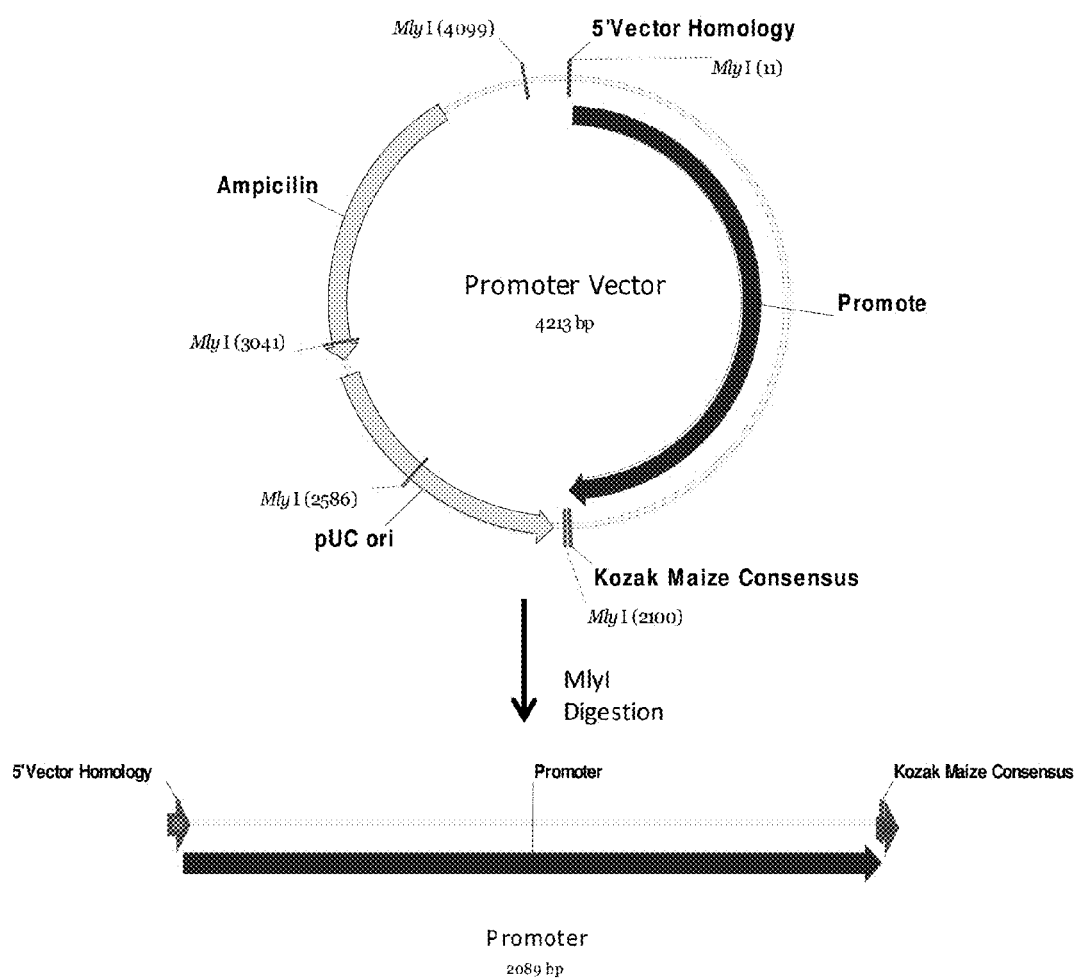
FIG. 6 shows an exemplary fragment 1 (promoter fragment) digested from a first DNA molecule (promoter vector). The fragment 1 comprises a Kozak sequence at its 3' end.
Figure 7:
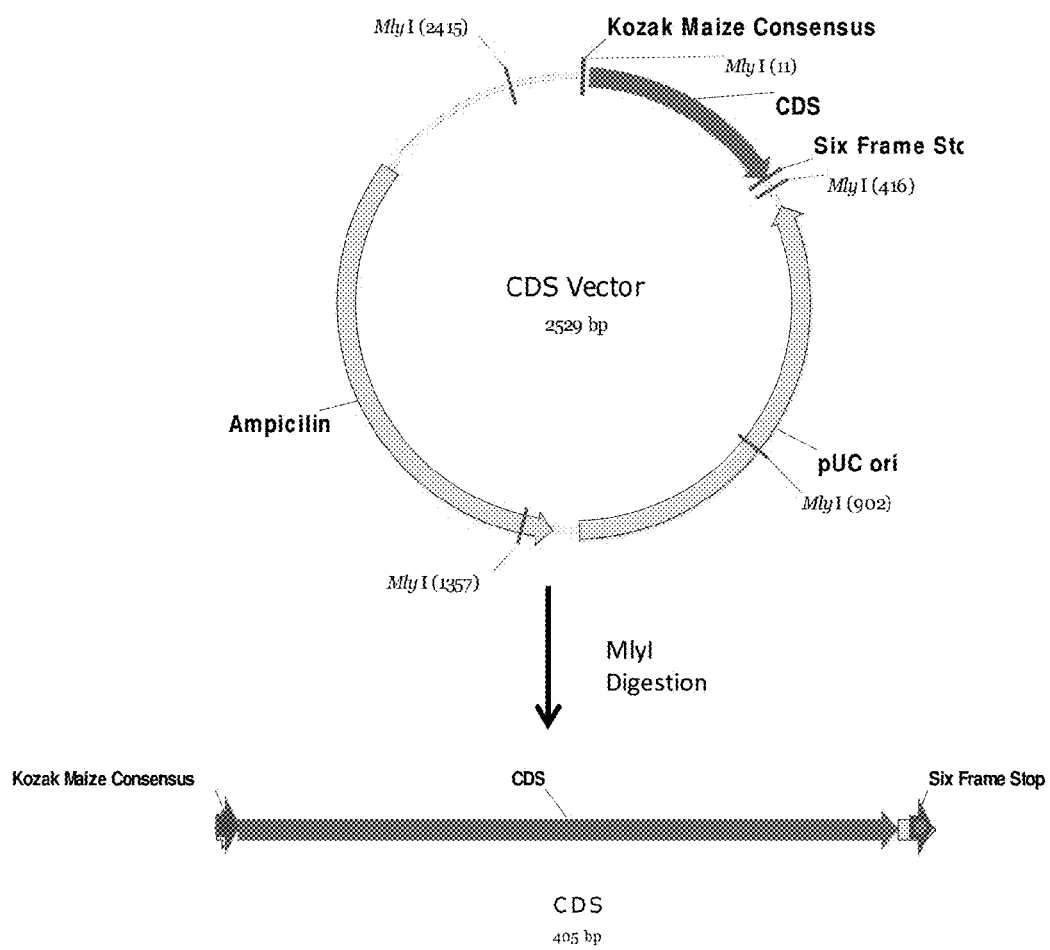
FIG. 7 shows an exemplary fragment 2 (coding sequence fragment) digested from a second DNA molecule (CDS vector). The fragment 2 comprises a Kozak sequence at its 5' end and a six frame stop sequence at its 3' end.
Figure 8:
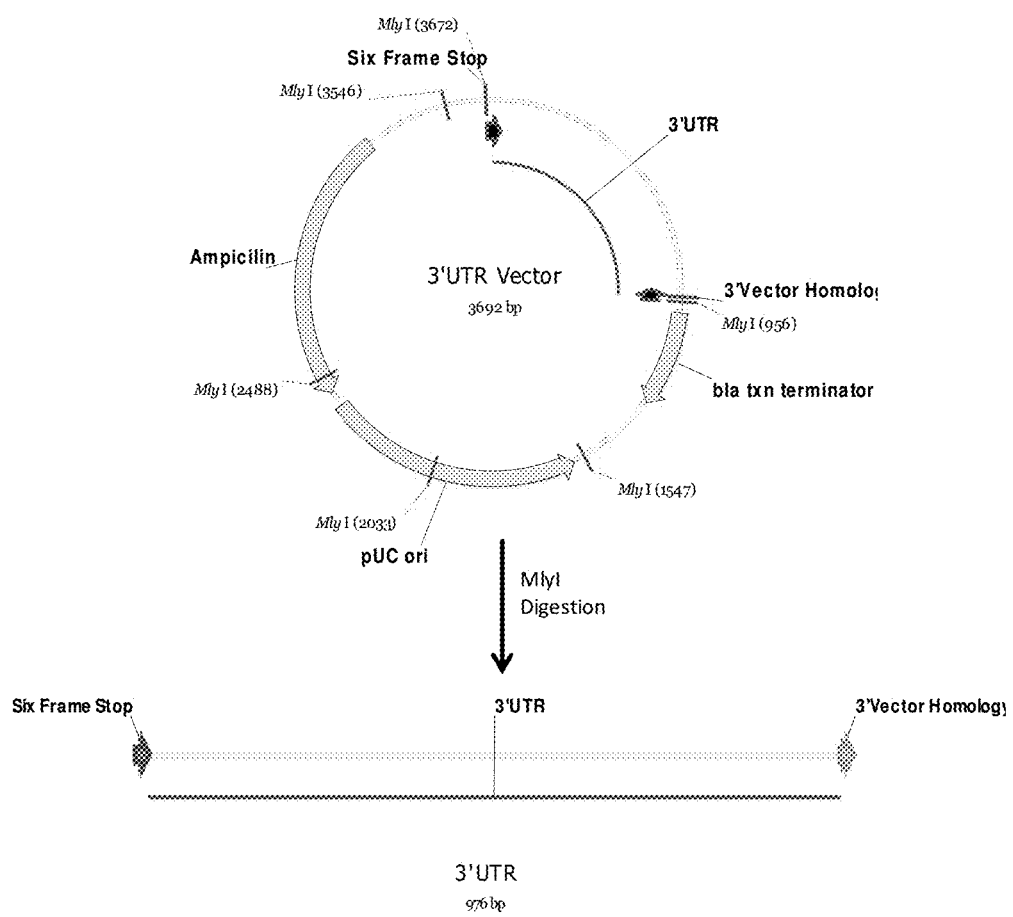
FIG. 8 shows an exemplary fragment 3 (3'UTR fragment) digested from a third DNA molecule (3'UTR vector). The fragment 3 comprises a six frame stop sequence at its 5' end.

FIG. 2B further shows another embodiment where DNA fragments are generated from restriction enzyme digestion with precursor plasmids, where DNA amplification including PCR is not used for vector assembly.

In some embodiments, the matching plasmid sequences is restriction enzyme (RE) recognition sites, which can be utilized for downstream analysis, either PTU or integration, once a transgene is inserted into the organism of interest. The RE sites could also be used for the recovery of DNA fragments from plasmids and its subsequent use in other vector assembly.

Figure 9:
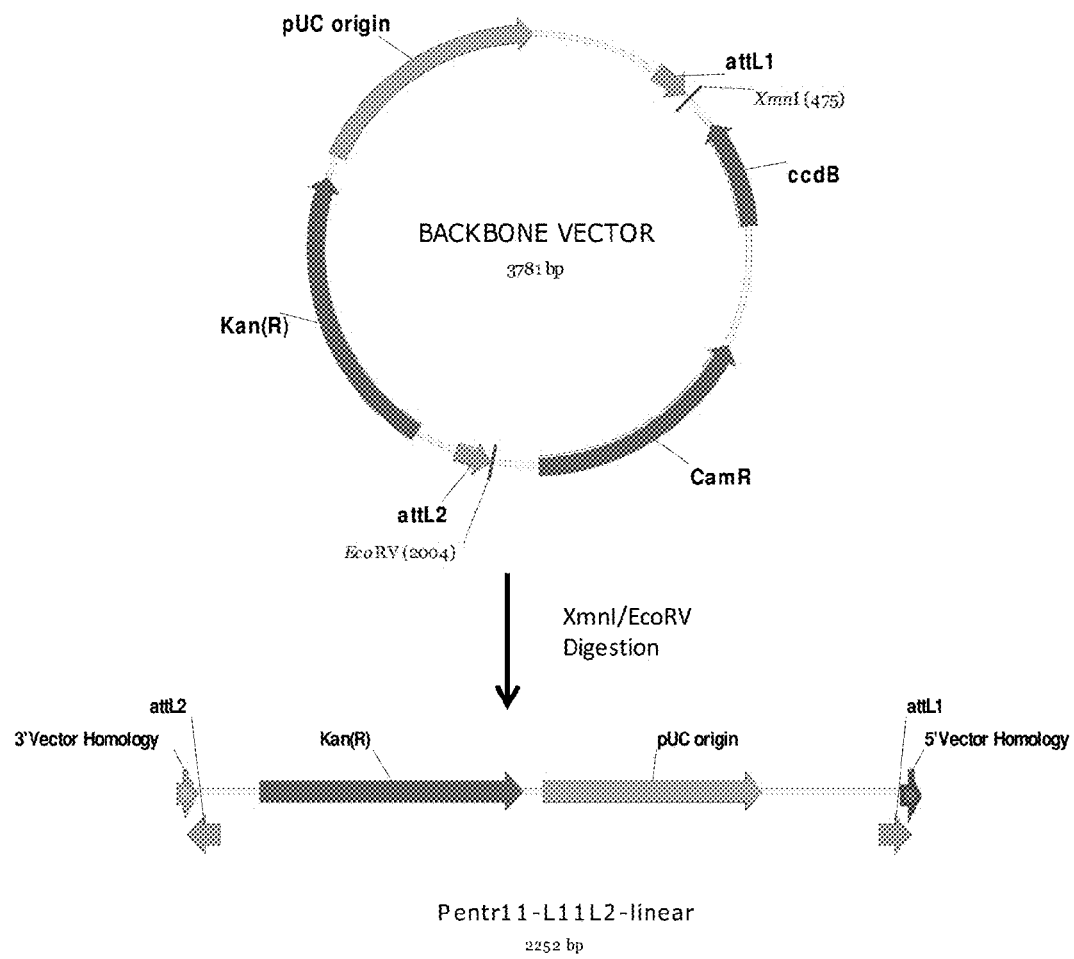
FIG. 9 shows an exemplary fragment 4 (3'UTR fragment) digested from a forth DNA molecule (backbone vector).

FIGS. 6-9 and 11 shows a specific embodiment according to FIG. 2B. The linear backbone is obtained deleting the ccdB gene using EcoRV/XmnI digestion of a backbone vector that contains Kanamycin selection gene (FIG. 9). A minimum 13 nucleotide Kozak sequence is inserted 5' while six frame stop codon is added on 3' of the coding sequence. The promoter contains Kozak sequence at the 3' junction and minimum 13 nucleotide sequence (5' vector homology) matching the plasmid junction. Similarly six frame stop codon sequence is inserted at the 5' end of 3' UTR. The 3' end of the 3'UTR contains 15 nucleotide sequence (3' vector homology) matching another end of the plasmid. The fragments are flanked by type II restriction sites such that no site is present within the fragment sequence. Type II enzyme can be chosen from AcuI, BciVI, BmrI, BseRI, BsrDI, BtsI, MlyI, and combinations thereof. Specifically, the promoter, CDS and 3'UTR containing required short homologies for vector assembly are flanked by type II restriction enzyme MlyI. The plasmids are restricted with MlyI and assembled vector of expected sizes are obtained. Theses assembled vectors can be verified by various restriction enzyme digestions followed by gel electrophoresis using methods well known in the art. Combining these modular linear fragments in the presence of suitable DNA recombination system can precisely assemble final vector containing four fragments in defined order without any undesired sequences within the transcription unit. The sequence of the assembled vector can also be verified by DNA sequencing.

Although the foregoing invention has been described in some detail by way of illustration and example for purposes of clarity of understanding, it will be obvious that certain changes and modifications may be practiced within the scope of the appended claims.

Example 2

Figure 10A:
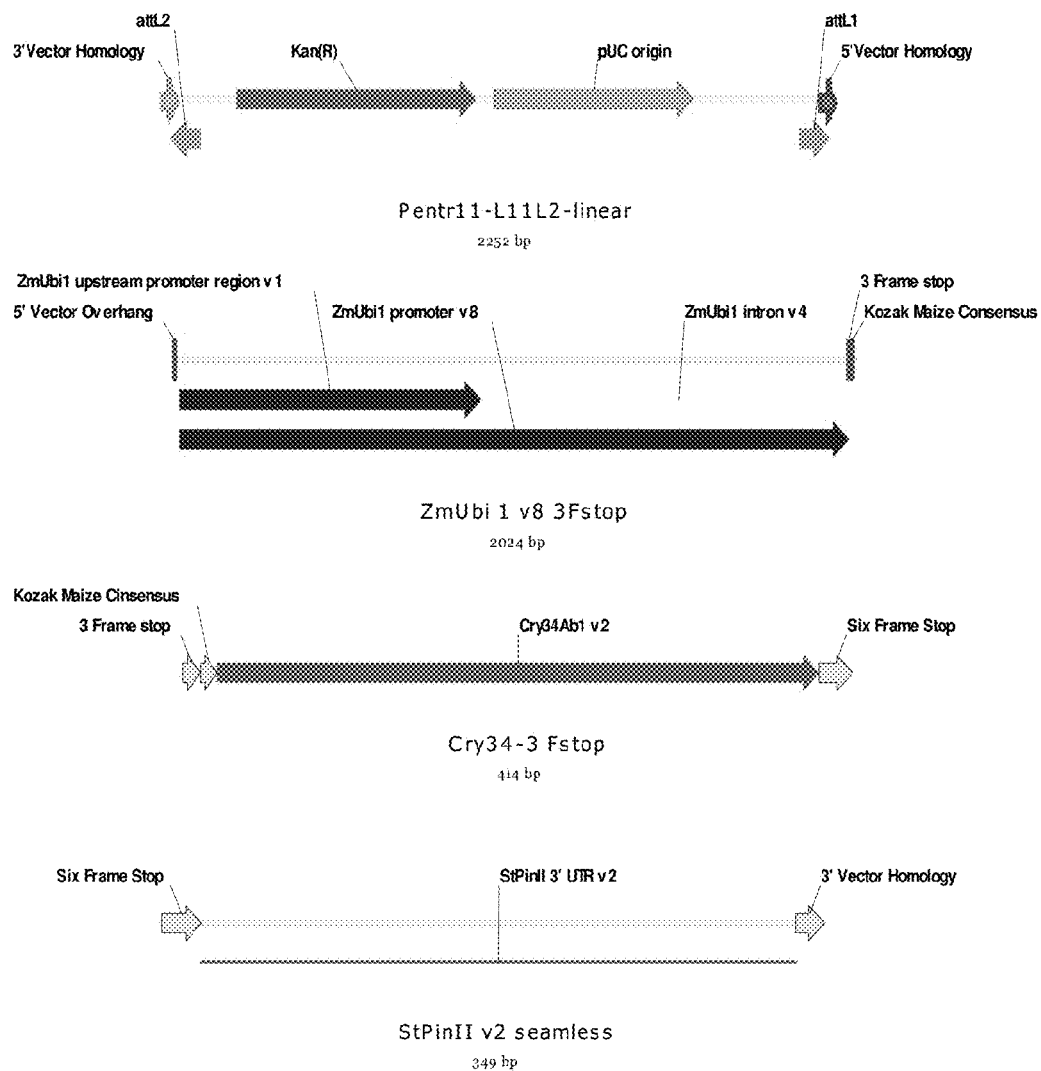
FIGS. 10A and 10B show another exemplary vector assembly using methods and/or systems provided herein.
Figure 10B:
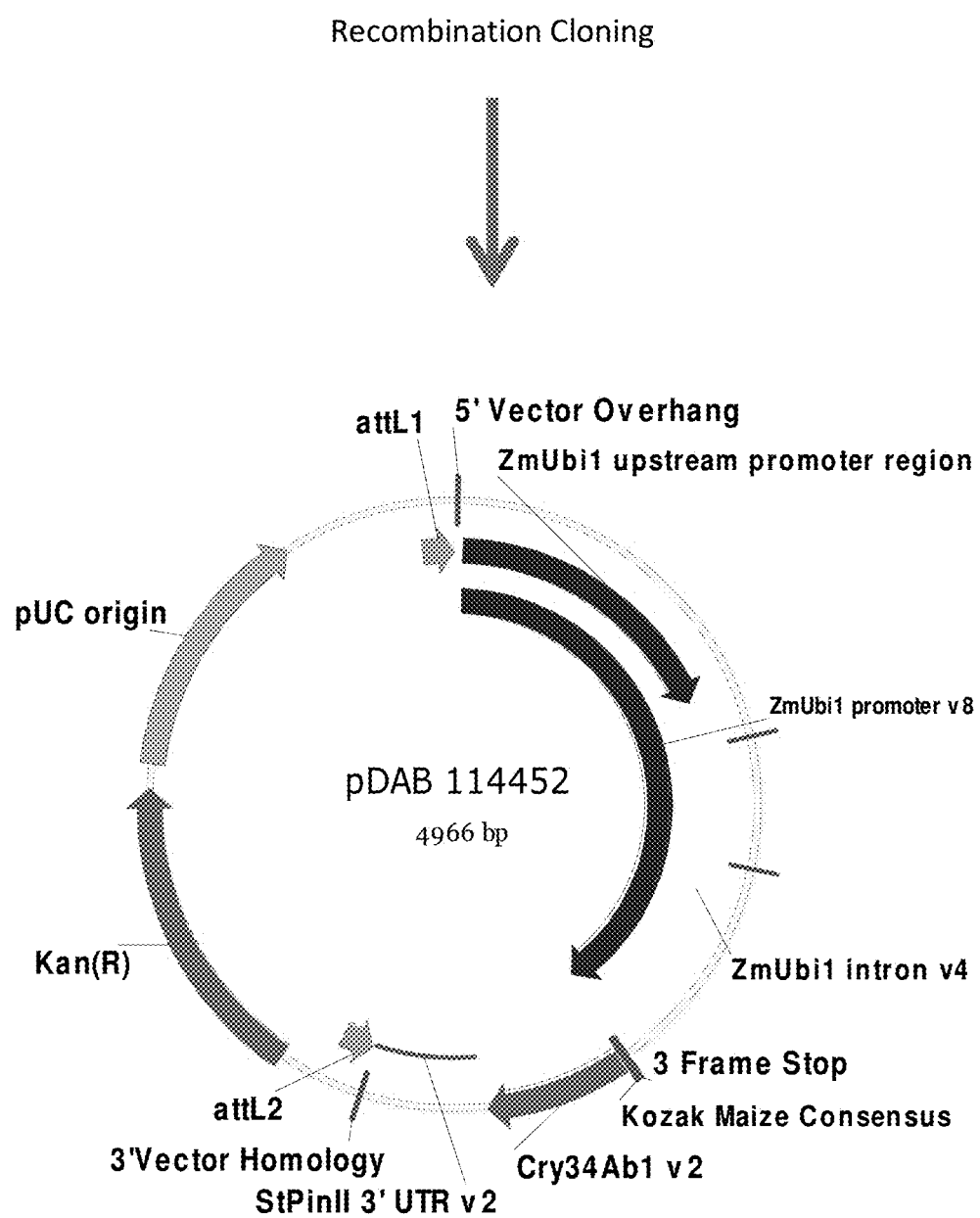

FIGS. 10A and 10B show another embodiment where promoter and CDS contain a Kozak sequence comprising a three-frame stop sequence at its 5' end. The linear backbone is obtained deleting the ccdB gene using EcoRV/XmnI digestion of a backbone vector that contains Kanamycin selection gene (for example FIG. 9). An eleven nucleotide three-frame stop sequence is added at 5' end of the ten nucleotide Kozak sequence that is inserted at 5' of the coding sequence (Cry34Ab1 v2), while a six frame stop codon sequence is added on 3' of the coding sequence.

The promoter (ZmUbi1 v8) also contains similar Kozak sequence comprising a three-frame stop sequence at the 3' junction and minimum thirteen nucleotide sequence (5' vector homology) matching the plasmid junction. Similarly six frame stop codon sequence is inserted at the 5' end of 3'

UTR (StPinII 3'UTR). The 3' end of the 3' UTR contains fifteen nucleotide sequence (3' vector homology) matching another end of the plasmid. The fragments are flanked by type II restriction sites such that no site is present within the fragment sequence. Type II enzyme can be chosen from for example AcuI, BciVI, BmrI, BseRI, BsrDI, BtsI, MlyI, and combinations thereof. Theses assembled vectors can be verified by various restriction enzyme digestions, and the fragment patterns after digestion to be observed using gel electrophoresis as well known in the art. The sequence of the assembled vector can also be verified by DNA sequencing using methods known in the art.

We claim:

1. A method for DNA assembly, comprising,
    (a) providing a first DNA molecule comprising a Kozak sequence, wherein the Kozak sequence is selected from the group consisting of SEQ ID NOs: 1-43 and 64-74;
    (b) providing a second DNA molecule comprising the same Kozak sequence of step (a) at one end and a six frame stop sequence at the other end, wherein the six frame stop sequence is selected from the group consisting of SEQ ID NOs: 75-80;
    (c) providing a third DNA molecule comprising the same six frame stop sequence of step (b);
    (d) providing a fourth DNA molecule comprising a linear vector sequence; and
    (e) assembling a product vector using the DNA molecules of steps (a), (b), (c), and (d) in the presence of at least one recombinase, where the Kozak sequence and the six frame stop sequence provide junction homologies for DNA recombination and wherein the product vector has sequences in the order of the DNA molecules from steps (a), (b), (c), and (d).

2. The method of claim 1, wherein the DNA molecules of steps (a), (b), (c), and (d) are obtained using PCR amplification or direct DNA synthesis.

3. The method of claim 1, wherein no DNA amplification technique is used.

4. The method of claim 1, wherein polymerase chain reaction is not used.

5. The method of claim 1, wherein the fourth DNA molecule comprises a lethal gene.

6. The method of claim 5, wherein the lethal gene is ccdB.

7. The method of claim 1, wherein the same Kozak sequence of both step (a) and (b) comprises a same three-frame stop sequence at its 5' end.

8. The method of claim 7, wherein the three-frame stop sequence is selected from the group consisting of SEQ ID NOS 44-62.

* * * * *

```
                          SEQUENCE LISTING

<160> NUMBER OF SEQ ID NOS: 88

<210> SEQ ID NO 1
<211> LENGTH: 15
<212> TYPE: DNA
<213> ORGANISM: Artificial Sequence
<220> FEATURE:
<223> OTHER INFORMATION: Kozak Sequence

<400> SEQUENCE: 1
ccacacgaca ccatg                                                      15

<210> SEQ ID NO 2
<211> LENGTH: 15
<212> TYPE: DNA
<213> ORGANISM: Artificial Sequence
<220> FEATURE:
<223> OTHER INFORMATION: Kozak Sequence

<400> SEQUENCE: 2
ccagaagaca ccatg                                                      15

<210> SEQ ID NO 3
<211> LENGTH: 15
<212> TYPE: DNA
<213> ORGANISM: Artificial Sequence
<220> FEATURE:
<223> OTHER INFORMATION: Kozak Sequence

<400> SEQUENCE: 3
aaagagcccg ccatg                                                      15

<210> SEQ ID NO 4
<211> LENGTH: 15
<212> TYPE: DNA
<213> ORGANISM: Artificial Sequence
<220> FEATURE:
<223> OTHER INFORMATION: Kozak Sequence

<400> SEQUENCE: 4
aaccgcccag ccatg                                                      15

<210> SEQ ID NO 5
<211> LENGTH: 15
<212> TYPE: DNA
<213> ORGANISM: Artificial Sequence
<220> FEATURE:
<223> OTHER INFORMATION: Kozak Sequence

<400> SEQUENCE: 5
aacgagaccg agatg                                                      15

<210> SEQ ID NO 6
<211> LENGTH: 15
<212> TYPE: DNA
<213> ORGANISM: Artificial Sequence
<220> FEATURE:
<223> OTHER INFORMATION: Kozak Sequence

<400> SEQUENCE: 6
```
aagagcccca agatg                                                    15

<210> SEQ ID NO 7
<211> LENGTH: 15
<212> TYPE: DNA
<213> ORGANISM: Artificial Sequence
<220> FEATURE:
<223> OTHER INFORMATION: Kozak Sequence

<400> SEQUENCE: 7
acaagagcca ccatg                                                    15

<210> SEQ ID NO 8
<211> LENGTH: 15
<212> TYPE: DNA
<213> ORGANISM: Artificial Sequence
<220> FEATURE:
<223> OTHER INFORMATION: Kozak Sequence

<400> SEQUENCE: 8
acaggaacca cgatg                                                    15

<210> SEQ ID NO 9
<211> LENGTH: 15
<212> TYPE: DNA
<213> ORGANISM: Artificial Sequence
<220> FEATURE:
<223> OTHER INFORMATION: Kozak Sequence

<400> SEQUENCE: 9
acccacgcag agatg                                                    15

<210> SEQ ID NO 10
<211> LENGTH: 15
<212> TYPE: DNA
<213> ORGANISM: Artificial Sequence
<220> FEATURE:
<223> OTHER INFORMATION: Kozak Sequence

<400> SEQUENCE: 10
agaacgacaa agatg                                                    15

<210> SEQ ID NO 11
<211> LENGTH: 15
<212> TYPE: DNA
<213> ORGANISM: Artificial Sequence
<220> FEATURE:
<223> OTHER INFORMATION: Kozak Sequence

<400> SEQUENCE: 11
agccgaacaa ccatg                                                    15

<210> SEQ ID NO 12
<211> LENGTH: 15
<212> TYPE: DNA
<213> ORGANISM: Artificial Sequence
<220> FEATURE:
<223> OTHER INFORMATION: Kozak Sequence

<400> SEQUENCE: 12
agccgaacaa cgatg                                                    15

<210> SEQ ID NO 13
<211> LENGTH: 15
<212> TYPE: DNA

```
<213> ORGANISM: Artificial Sequence
<220> FEATURE:
<223> OTHER INFORMATION: Kozak Sequence

<400> SEQUENCE: 13
caaaggcccg ccatg                                                        15

<210> SEQ ID NO 14
<211> LENGTH: 15
<212> TYPE: DNA
<213> ORGANISM: Artificial Sequence
<220> FEATURE:
<223> OTHER INFORMATION: Kozak Sequence

<400> SEQUENCE: 14
caacgcccag ccatg                                                        15

<210> SEQ ID NO 15
<211> LENGTH: 15
<212> TYPE: DNA
<213> ORGANISM: Artificial Sequence
<220> FEATURE:
<223> OTHER INFORMATION: Kozak Sequence

<400> SEQUENCE: 15
cacagccccg agatg                                                        15

<210> SEQ ID NO 16
<211> LENGTH: 15
<212> TYPE: DNA
<213> ORGANISM: Artificial Sequence
<220> FEATURE:
<223> OTHER INFORMATION: Kozak Sequence

<400> SEQUENCE: 16
cacggaacca agatg                                                        15

<210> SEQ ID NO 17
<211> LENGTH: 15
<212> TYPE: DNA
<213> ORGANISM: Artificial Sequence
<220> FEATURE:
<223> OTHER INFORMATION: Kozak Sequence

<400> SEQUENCE: 17
cagacagcca ccatg                                                        15

<210> SEQ ID NO 18
<211> LENGTH: 15
<212> TYPE: DNA
<213> ORGANISM: Artificial Sequence
<220> FEATURE:
<223> OTHER INFORMATION: Kozak Sequence

<400> SEQUENCE: 18 cagacccccca cgatg                                                       15

<210> SEQ ID NO 19
<211> LENGTH: 15
<212> TYPE: DNA
<213> ORGANISM: Artificial Sequence
<220> FEATURE:
<223> OTHER INFORMATION: Kozak Sequence

<400> SEQUENCE: 19
caggcgtcag agatg                                                        15
```

<210> SEQ ID NO 20
<211> LENGTH: 15
<212> TYPE: DNA
<213> ORGANISM: Artificial Sequence
<220> FEATURE:
<223> OTHER INFORMATION: Kozak Sequence

<400> SEQUENCE: 20
cagtggccaa agatg                                                      15

<210> SEQ ID NO 21
<211> LENGTH: 15
<212> TYPE: DNA
<213> ORGANISM: Artificial Sequence
<220> FEATURE:
<223> OTHER INFORMATION: Kozak Sequence

<400> SEQUENCE: 21
ccaccagcaa ccatg                                                      15

<210> SEQ ID NO 22
<211> LENGTH: 15
<212> TYPE: DNA
<213> ORGANISM: Artificial Sequence
<220> FEATURE:
<223> OTHER INFORMATION: Kozak Sequence

<400> SEQUENCE: 22
ccccaagcaa cgatg                                                      15

<210> SEQ ID NO 23
<211> LENGTH: 15
<212> TYPE: DNA
<213> ORGANISM: Artificial Sequence
<220> FEATURE:
<223> OTHER INFORMATION: Kozak Sequence

<400> SEQUENCE: 23
cccgacaccg ccatg                                                      15

<210> SEQ ID NO 24
<211> LENGTH: 15
<212> TYPE: DNA
<213> ORGANISM: Artificial Sequence
<220> FEATURE:
<223> OTHER INFORMATION: Kozak Sequence

<400> SEQUENCE: 24
cgcaccacag ccatg                                                      15

<210> SEQ ID NO 25
<211> LENGTH: 15
<212> TYPE: DNA
<213> ORGANISM: Artificial Sequence
<220> FEATURE:
<223> OTHER INFORMATION: Kozak Sequence

<400> SEQUENCE: 25
cgggtcaccg agatg                                                      15

<210> SEQ ID NO 26
<211> LENGTH: 15
<212> TYPE: DNA
<213> ORGANISM: Artificial Sequence
<220> FEATURE:

```
<223> OTHER INFORMATION: Kozak Sequence

<400> SEQUENCE: 26
gaaagaccca agatg                                                    15

<210> SEQ ID NO 27
<211> LENGTH: 15
<212> TYPE: DNA
<213> ORGANISM: Artificial Sequence
<220> FEATURE:
<223> OTHER INFORMATION: Kozak Sequence

<400> SEQUENCE: 27
gaagacacca ccatg                                                    15

<210> SEQ ID NO 28
<211> LENGTH: 15
<212> TYPE: DNA
<213> ORGANISM: Artificial Sequence
<220> FEATURE:
<223> OTHER INFORMATION: Kozak Sequence

<400> SEQUENCE: 28
gacacagcca cgatg                                                    15

<210> SEQ ID NO 29
<211> LENGTH: 15
<212> TYPE: DNA
<213> ORGANISM: Artificial Sequence
<220> FEATURE:
<223> OTHER INFORMATION: Kozak Sequence

<400> SEQUENCE: 29
gcaaagacag agatg                                                    15

<210> SEQ ID NO 30
<211> LENGTH: 15
<212> TYPE: DNA
<213> ORGANISM: Artificial Sequence
<220> FEATURE:
<223> OTHER INFORMATION: Kozak Sequence

<400> SEQUENCE: 30
gcaaagacaa agatg                                                    15

<210> SEQ ID NO 31
<211> LENGTH: 15
<212> TYPE: DNA
<213> ORGANISM: Artificial Sequence
<220> FEATURE:
<223> OTHER INFORMATION: Kozak Sequence

<400> SEQUENCE: 31
gccaccacaa ccatg                                                    15

<210> SEQ ID NO 32
<211> LENGTH: 15
<212> TYPE: DNA
<213> ORGANISM: Artificial Sequence
<220> FEATURE:
<223> OTHER INFORMATION: Kozak Sequence

<400> SEQUENCE: 32
gcgaaaacaa cgatg                                                    15
```

```
<210> SEQ ID NO 33
<211> LENGTH: 15
<212> TYPE: DNA
<213> ORGANISM: Artificial Sequence
<220> FEATURE:
<223> OTHER INFORMATION: Kozak Sequence

<400> SEQUENCE: 33
gcgcgtaccg ccatg                                                    15

<210> SEQ ID NO 34
<211> LENGTH: 15
<212> TYPE: DNA
<213> ORGANISM: Artificial Sequence
<220> FEATURE:
<223> OTHER INFORMATION: Kozak Sequence

<400> SEQUENCE: 34
ggaaccacag ccatg                                                    15

<210> SEQ ID NO 35
<211> LENGTH: 15
<212> TYPE: DNA
<213> ORGANISM: Artificial Sequence
<220> FEATURE:
<223> OTHER INFORMATION: Kozak Sequence

<400> SEQUENCE: 35
ggcacaaccg agatg                                                    15

<210> SEQ ID NO 36
<211> LENGTH: 15
<212> TYPE: DNA
<213> ORGANISM: Artificial Sequence
<220> FEATURE:
<223> OTHER INFORMATION: Kozak Sequence

<400> SEQUENCE: 36
ggccaaacca agatg                                                    15

<210> SEQ ID NO 37
<211> LENGTH: 15
<212> TYPE: DNA
<213> ORGANISM: Artificial Sequence
<220> FEATURE:
<223> OTHER INFORMATION: Kozak Sequence

<400> SEQUENCE: 37
ggctagccca ccatg                                                    15

<210> SEQ ID NO 38
<211> LENGTH: 15
<212> TYPE: DNA
<213> ORGANISM: Artificial Sequence
<220> FEATURE:
<223> OTHER INFORMATION: Kozak Sequence

<400> SEQUENCE: 38
gggcatccca cgatg                                                    15

<210> SEQ ID NO 39
<211> LENGTH: 15
<212> TYPE: DNA
<213> ORGANISM: Artificial Sequence
<220> FEATURE:
<223> OTHER INFORMATION: Kozak Sequence
```

```
<400> SEQUENCE: 39
ggtgcaccag agatg                                               15

<210> SEQ ID NO 40
<211> LENGTH: 15
<212> TYPE: DNA
<213> ORGANISM: Artificial Sequence
<220> FEATURE:
<223> OTHER INFORMATION: Kozak Sequence

<400> SEQUENCE: 40
gtcagcgcaa agatg                                               15

<210> SEQ ID NO 41
<211> LENGTH: 15
<212> TYPE: DNA
<213> ORGANISM: Artificial Sequence
<220> FEATURE:
<223> OTHER INFORMATION: Kozak Sequence

<400> SEQUENCE: 41
tgcggcacaa ccatg                                               15

<210> SEQ ID NO 42
<211> LENGTH: 15
<212> TYPE: DNA
<213> ORGANISM: Artificial Sequence
<220> FEATURE:
<223> OTHER INFORMATION: Kozak Sequence

<400> SEQUENCE: 42
tgggacccaa cgatg                                               15

<210> SEQ ID NO 43
<211> LENGTH: 15
<212> TYPE: DNA
<213> ORGANISM: Artificial Sequence
<220> FEATURE:
<223> OTHER INFORMATION: Kozak Sequence

<400> SEQUENCE: 43
ccggggtcga ccatg                                               15

<210> SEQ ID NO 44
<211> LENGTH: 11
<212> TYPE: DNA
<213> ORGANISM: Artificial Sequence
<220> FEATURE:
<223> OTHER INFORMATION: 3-Frame Stop

<400> SEQUENCE: 44
taattaattg a                                                   11

<210> SEQ ID NO 45
<211> LENGTH: 11
<212> TYPE: DNA
<213> ORGANISM: Artificial Sequence
<220> FEATURE:
<223> OTHER INFORMATION: 3-Frame Stop

<400> SEQUENCE: 45
taattagtta a                                                   11

<210> SEQ ID NO 46
<211> LENGTH: 11
```

```
<212> TYPE: DNA
<213> ORGANISM: Artificial Sequence
<220> FEATURE:
<223> OTHER INFORMATION: 3-Frame Stop

<400> SEQUENCE: 46
taattagtta g                                                            11

<210> SEQ ID NO 47
<211> LENGTH: 11
<212> TYPE: DNA
<213> ORGANISM: Artificial Sequence
<220> FEATURE:
<223> OTHER INFORMATION: 3-Frame Stop

<400> SEQUENCE: 47
taattagttg a                                                            11

<210> SEQ ID NO 48
<211> LENGTH: 11
<212> TYPE: DNA
<213> ORGANISM: Artificial Sequence
<220> FEATURE:
<223> OTHER INFORMATION: 3-Frame Stop

<400> SEQUENCE: 48
taattgattg a                                                            11

<210> SEQ ID NO 49
<211> LENGTH: 11
<212> TYPE: DNA
<213> ORGANISM: Artificial Sequence
<220> FEATURE:
<223> OTHER INFORMATION: 3-Frame Stop

<400> SEQUENCE: 49
tagttaatta a                                                            11

<210> SEQ ID NO 50
<211> LENGTH: 11
<212> TYPE: DNA
<213> ORGANISM: Artificial Sequence
<220> FEATURE:
<223> OTHER INFORMATION: 3-Frame Stop

<400> SEQUENCE: 50
tagttaatta g                                                            11

<210> SEQ ID NO 51
<211> LENGTH: 11
<212> TYPE: DNA
<213> ORGANISM: Artificial Sequence
<220> FEATURE:
<223> OTHER INFORMATION: 3-Frame Stop

<400> SEQUENCE: 51
tagttaattg a                                                            11

<210> SEQ ID NO 52
<211> LENGTH: 11
<212> TYPE: DNA
<213> ORGANISM: Artificial Sequence
<220> FEATURE:
<223> OTHER INFORMATION: 3-Frame Stop

<400> SEQUENCE: 52
```
tagttagtta a          11

<210> SEQ ID NO 53
<211> LENGTH: 11
<212> TYPE: DNA
<213> ORGANISM: Artificial Sequence
<220> FEATURE:
<223> OTHER INFORMATION: 3-Frame Stop

<400> SEQUENCE: 53
tagttagtta g          11

<210> SEQ ID NO 54
<211> LENGTH: 11
<212> TYPE: DNA
<213> ORGANISM: Artificial Sequence
<220> FEATURE:
<223> OTHER INFORMATION: 3-Frame Stop

<400> SEQUENCE: 54
tagttagttg a          11

<210> SEQ ID NO 55
<211> LENGTH: 11
<212> TYPE: DNA
<213> ORGANISM: Artificial Sequence
<220> FEATURE:
<223> OTHER INFORMATION: 3-Frame Stop

<400> SEQUENCE: 55
tagttgatta a          11

<210> SEQ ID NO 56
<211> LENGTH: 11
<212> TYPE: DNA
<213> ORGANISM: Artificial Sequence
<220> FEATURE:
<223> OTHER INFORMATION: 3-Frame Stop

<400> SEQUENCE: 56
tagttgatta g          11

<210> SEQ ID NO 57
<211> LENGTH: 11
<212> TYPE: DNA
<213> ORGANISM: Artificial Sequence
<220> FEATURE:
<223> OTHER INFORMATION: 3-Frame Stop

<400> SEQUENCE: 57
tagttgattg a          11

<210> SEQ ID NO 58
<211> LENGTH: 11
<212> TYPE: DNA
<213> ORGANISM: Artificial Sequence
<220> FEATURE:
<223> OTHER INFORMATION: 3-Frame Stop

<400> SEQUENCE: 58
tgattaattg a          11

<210> SEQ ID NO 59
<211> LENGTH: 11
<212> TYPE: DNA
<213> ORGANISM: Artificial Sequence

```
<220> FEATURE:
<223> OTHER INFORMATION: 3-Frame Stop

<400> SEQUENCE: 59
tgattagtta a                                                          11

<210> SEQ ID NO 60
<211> LENGTH: 11
<212> TYPE: DNA
<213> ORGANISM: Artificial Sequence
<220> FEATURE:
<223> OTHER INFORMATION: 3-Frame Stop

<400> SEQUENCE: 60
tgattagtta g                                                          11

<210> SEQ ID NO 61
<211> LENGTH: 11
<212> TYPE: DNA
<213> ORGANISM: Artificial Sequence
<220> FEATURE:
<223> OTHER INFORMATION: 3-Frame Stop

<400> SEQUENCE: 61
tgattagttg a                                                          11

<210> SEQ ID NO 62
<211> LENGTH: 11
<212> TYPE: DNA
<213> ORGANISM: Artificial Sequence
<220> FEATURE:
<223> OTHER INFORMATION: 3-Frame Stop

<400> SEQUENCE: 62
tgattgattg a                                                          11

<210> SEQ ID NO 63
<211> LENGTH: 24
<212> TYPE: DNA
<213> ORGANISM: Artificial Sequence
<220> FEATURE:
<223> OTHER INFORMATION: Kozak Sequence

<400> SEQUENCE: 63
tagttagttg aacacgacac catg                                            24

<210> SEQ ID NO 64
<211> LENGTH: 15
<212> TYPE: DNA
<213> ORGANISM: Artificial Sequence
<220> FEATURE:
<223> OTHER INFORMATION: Kozak Sequence

<400> SEQUENCE: 64
ctgcaggtcg acatg                                                      15

<210> SEQ ID NO 65
<211> LENGTH: 15
<212> TYPE: DNA
<213> ORGANISM: Artificial Sequence
<220> FEATURE:
<223> OTHER INFORMATION: Kozak Sequence

<400> SEQUENCE: 65
ctgcaggtcg acatg                                                      15
```

```
<210> SEQ ID NO 66
<211> LENGTH: 19
<212> TYPE: DNA
<213> ORGANISM: Artificial Sequence
<220> FEATURE:
<223> OTHER INFORMATION: Kozak Sequence

<400> SEQUENCE: 66
aagtttgtag atctccatg                                                    19

<210> SEQ ID NO 67
<211> LENGTH: 19
<212> TYPE: DNA
<213> ORGANISM: Artificial Sequence
<220> FEATURE:
<223> OTHER INFORMATION: Kozak Sequence

<400> SEQUENCE: 67
aaatgcgcag atccccatg                                                    19

<210> SEQ ID NO 68
<211> LENGTH: 8
<212> TYPE: DNA
<213> ORGANISM: Artificial Sequence
<220> FEATURE:
<223> OTHER INFORMATION: Kozak Sequence

<400> SEQUENCE: 68 aaaaaatg                                                                 8

<210> SEQ ID NO 69
<211> LENGTH: 8
<212> TYPE: DNA
<213> ORGANISM: Artificial Sequence
<220> FEATURE:
<223> OTHER INFORMATION: Kozak Sequence

<400> SEQUENCE: 69 caaaaatg                                                                 8

<210> SEQ ID NO 70
<211> LENGTH: 8
<212> TYPE: DNA
<213> ORGANISM: Artificial Sequence
<220> FEATURE:
<223> OTHER INFORMATION: Kozak Sequence

<400> SEQUENCE: 70 aaaacatg                                                                 8

<210> SEQ ID NO 71
<211> LENGTH: 8
<212> TYPE: DNA
<213> ORGANISM: Artificial Sequence
<220> FEATURE:
<223> OTHER INFORMATION: Kozak Sequence

<400> SEQUENCE: 71 caaacatg                                                                 8

<210> SEQ ID NO 72
<211> LENGTH: 8
<212> TYPE: DNA
<213> ORGANISM: Artificial Sequence
<220> FEATURE:
<223> OTHER INFORMATION: Kozak Sequence
```

```
<400> SEQUENCE: 72 aacaaatg                                                                    8

<210> SEQ ID NO 73
<211> LENGTH: 8
<212> TYPE: DNA
<213> ORGANISM: Artificial Sequence
<220> FEATURE:
<223> OTHER INFORMATION: Kozak Sequence

<400> SEQUENCE: 73 aaacaatg                                                                    8

<210> SEQ ID NO 74
<211> LENGTH: 8
<212> TYPE: DNA
<213> ORGANISM: Artificial Sequence
<220> FEATURE:
<223> OTHER INFORMATION: Kozak Sequence

<400> SEQUENCE: 74 aaccaatg                                                                    8

<210> SEQ ID NO 75
<211> LENGTH: 29
<212> TYPE: DNA
<213> ORGANISM: Artificial Sequence
<220> FEATURE:
<223> OTHER INFORMATION: 6-Frame Stop

<400> SEQUENCE: 75
tgagtagtta gcttaatcac ctagagctc                                            29

<210> SEQ ID NO 76
<211> LENGTH: 29
<212> TYPE: DNA
<213> ORGANISM: Artificial Sequence
<220> FEATURE:
<223> OTHER INFORMATION: 6-Frame Stop

<400> SEQUENCE: 76
taggtagtta gcttaatcac ctagagctc                                            29

<210> SEQ ID NO 77
<211> LENGTH: 29
<212> TYPE: DNA
<213> ORGANISM: Artificial Sequence
<220> FEATURE:
<223> OTHER INFORMATION: 6-Frame Stop

<400> SEQUENCE: 77
taggtaatta gcttaatcac ctagagctc                                            29

<210> SEQ ID NO 78
<211> LENGTH: 29
<212> TYPE: DNA
<213> ORGANISM: Artificial Sequence
<220> FEATURE:
<223> OTHER INFORMATION: 6-Frame Stop

<400> SEQUENCE: 78
tgagtagtta gcttaatcac ctagagctc                                            29

<210> SEQ ID NO 79
```

```
<211> LENGTH: 29
<212> TYPE: DNA
<213> ORGANISM: Artificial Sequence
<220> FEATURE:
<223> OTHER INFORMATION: 6-Frame Stop

<400> SEQUENCE: 79
taagtagtta gcttaatcac ctagagctc                                    29

<210> SEQ ID NO 80
<211> LENGTH: 29
<212> TYPE: DNA
<213> ORGANISM: Artificial Sequence
<220> FEATURE:
<223> OTHER INFORMATION: 6-Frame Stop

<400> SEQUENCE: 80
tgagtaatta gcttaatcac ctagagctc                                    29

<210> SEQ ID NO 81
<211> LENGTH: 8
<212> TYPE: DNA
<213> ORGANISM: Artificial Sequence
<220> FEATURE:
<223> OTHER INFORMATION: Kozak Sequence

<400> SEQUENCE: 81 ccaccatg                                                            8

<210> SEQ ID NO 82
<211> LENGTH: 9
<212> TYPE: DNA
<213> ORGANISM: Artificial Sequence
<220> FEATURE:
<223> OTHER INFORMATION: Kozak sequence

<400> SEQUENCE: 82 ccaccatgg                                                           9

<210> SEQ ID NO 83
<211> LENGTH: 8
<212> TYPE: DNA
<213> ORGANISM: Artificial Sequence
<220> FEATURE:
<223> OTHER INFORMATION: Kozak sequence

<400> SEQUENCE: 83 ccaccatg                                                            8

<210> SEQ ID NO 84
<211> LENGTH: 9
<212> TYPE: DNA
<213> ORGANISM: Artificial Sequence
<220> FEATURE:
<223> OTHER INFORMATION: Kozak sequence

<400> SEQUENCE: 84 ccaccatgg                                                           9

<210> SEQ ID NO 85
<211> LENGTH: 12
<212> TYPE: DNA
<213> ORGANISM: Artificial Sequence
<220> FEATURE:
<223> OTHER INFORMATION: 6-Frame stop sequence
<220> FEATURE:
<221> NAME/KEY: misc_feature
```

```
<222> LOCATION: (10)..(10)
<223> OTHER INFORMATION: n is a, c, g, or t

<400> SEQUENCE: 85
ctaactaatn ag                                                          12

<210> SEQ ID NO 86
<211> LENGTH: 14
<212> TYPE: DNA
<213> ORGANISM: Artificial Sequence
<220> FEATURE:
<223> OTHER INFORMATION: 6-Frame stop sequence

<400> SEQUENCE: 86
ctagactagt ctag                                                        14

<210> SEQ ID NO 87
<211> LENGTH: 12
<212> TYPE: DNA
<213> ORGANISM: Artificial Sequence
<220> FEATURE:
<223> OTHER INFORMATION: 6-Frame stop sequence
<220> FEATURE:
<221> NAME/KEY: misc_feature
<222> LOCATION: (10)..(10)
<223> OTHER INFORMATION: n is a, c, g, or t

<400> SEQUENCE: 87
ctaactaatn ag                                                          12

<210> SEQ ID NO 88
<211> LENGTH: 14
<212> TYPE: DNA
<213> ORGANISM: Artificial Sequence
<220> FEATURE:
<223> OTHER INFORMATION: 6-Frame stop sequence

<400> SEQUENCE: 88
ctagactagt ctag                                                        14
```